United States Patent
Towe

(10) Patent No.: US 10,022,566 B2
(45) Date of Patent: Jul. 17, 2018

(54) APPARATUS, SYSTEMS, AND METHODS FOR CURRENT MONITORING IN ULTRASOUND POWERED NEUROSTIMULATION

(75) Inventor: Bruce C. Towe, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 224 days.

(21) Appl. No.: 13/819,922

(22) PCT Filed: Aug. 31, 2011

(86) PCT No.: PCT/US2011/049966
§ 371 (c)(1),
(2), (4) Date: Aug. 15, 2013

(87) PCT Pub. No.: WO2012/030962
PCT Pub. Date: Mar. 8, 2012

(65) Prior Publication Data
US 2013/0324891 A1    Dec. 5, 2013

Related U.S. Application Data

(60) Provisional application No. 61/378,716, filed on Aug. 31, 2010.

(51) Int. Cl.
*A61N 7/00*      (2006.01)
*A61N 1/36*      (2006.01)
(Continued)

(52) U.S. Cl.
CPC .......... *A61N 7/00* (2013.01); *A61N 1/36139* (2013.01); *A61N 1/3787* (2013.01); *A61N 1/37217* (2013.01); *A61N 2007/0026* (2013.01)

(58) Field of Classification Search
None
See application file for complete search history.

(56) References Cited

U.S. PATENT DOCUMENTS

| | | | |
|---|---|---|---|
| 3,735,756 A | 5/1973 | Richards et al. | 601/2 |
| 5,957,851 A | 9/1999 | Hossack | 600/459 |

(Continued)

FOREIGN PATENT DOCUMENTS

| | | |
|---|---|---|
| WO | WO 2004/105583 | 12/2004 |
| WO | WO 2010/027963 | 3/2010 |

OTHER PUBLICATIONS

Standard Curves (http://biology.kenyon.edu/courses/biol09/standard%curve/intro.htm, Jan. 2, 2004).*

(Continued)

*Primary Examiner* — Amelie R Gillman
*Assistant Examiner* — Carolyn Pehlke
(74) *Attorney, Agent, or Firm* — Norton Rose Fulbright US LLP

(57) ABSTRACT

Apparatus, systems, and methods for current monitoring in ultrasound powered neurostimulation. The apparatus may include an ultrasound transmitter configured to emit an ultrasound output directed at a piezoelectric device implanted in biological tissue. The apparatus may also include a detector configured to detect an induced current in response to the ultrasound output in the biological tissue. The piezoelectric device may include a piezoelectric material and a diode. The apparatus may include a feedback mechanism to control the amount of induced current in the biological tissue.

17 Claims, 5 Drawing Sheets

(51) Int. Cl.
*A61N 1/372* (2006.01)
*A61N 1/378* (2006.01)

(56) References Cited

U.S. PATENT DOCUMENTS

| | | | |
|---|---|---|---|
| 6,231,516 B1 | 5/2001 | Keilman et al. | 600/485 |
| 6,562,033 B2 | 5/2003 | Shah et al. | 606/41 |
| 6,647,296 B2 | 11/2003 | Fishell et al. | 607/45 |
| 7,702,395 B2 | 4/2010 | Towe et al. | 607/48 |
| 7,713,200 B1 * | 5/2010 | Sarvazyan et al. | 600/437 |
| 7,894,907 B2 | 2/2011 | Cowan et al. | 607/46 |
| 7,899,542 B2 | 3/2011 | Cowan et al. | 607/46 |
| 8,078,283 B2 | 12/2011 | Cowan et al. | 607/51 |
| 8,082,041 B1 * | 12/2011 | Radziemski | A61N 1/3787 607/33 |
| 2004/0172083 A1 | 9/2004 | Penner | 607/35 |
| 2005/0055073 A1 | 3/2005 | Weber | 607/99 |
| 2006/0167500 A1 | 7/2006 | Towe et al. | 607/3 |
| 2007/0276232 A1 | 11/2007 | Towe | 600/437 |
| 2008/0108915 A1 | 5/2008 | Penner | 601/2 |
| 2010/0249677 A1 * | 9/2010 | DiUbaldi et al. | 601/46 |
| 2013/0096435 A1 | 4/2013 | Towe | |

OTHER PUBLICATIONS

Jim Lesurf (Diode I/V Behavior, https://www.st-andrews.ac.uk/~www_pa/Scots_Guide/info/comp/passive/diode/chars/chars.htm, Jan. 3, 2003).*
Chemicals, the Environment, and You: Explorations in Science and Human Health (NIH Curriculumn Supplement, Lesson 3: Dose Response Relationships, 2000).*
Primer on Absolute vs. Relative Differences (Effective Clincal Practice, vol. 2, No. 6, Nov. 1999).*
Intro to Piezoelectric Transducer Crystals (http://bostonpiezooptics.com/intro-to-transducer-crystals, Sep. 7, 2013).*
Dealing with a Noisy Signal (Tektronix, http://www.tek.com/dl/DealingWithNoisySignal_ApplicationNote_3GW_22049_0.pdf, Oct. 2008).*
Avago (zero bias Schottky detector diode data sheet, http://www.avagotech.com/docs/AV02-1377EN, May 2009).*
The Master's thesis of Bioengineering student Mr. William Phillips, planned for May 2002 commencement and subsequent placement within a few months in ASU library.
An abstract submitted for review to the BMES Meeting in Houston, Texas, for presentation in Oct. of 2002.
Gavrilov et al., "Stimulation of human peripheral neural structures by focus ultrasound", *Sov. Phys. Acoust.*, 19(4):332-334, 1974.
Hu et al., "Effects of low-intensity ultrasound on the central nervous system of primates", *Avist Space Environ. Med.*, 47(60):640-643, 1976.
Talkagi et al., "The actions of ultrasound on the myelinated nerve, the spinal cord, and the brain", *Jpn. J. Physiol*, 10:183-193, 1959.
Mihran et al., "Temporally specific modifications of myelinated axon excitability in vitro following a single ultrasound pulse", *Ultrasound in Med. Biol.*, 16(3):297-309, 1990.
Velling et al., "Modulation of the functional state of the brain with aid of focused ultrasonic action," *Nurosci. Behav. Physiol*, 18(5):369-375, 1988.
Wells, P.N.T., Biomedical Ultrasonics, Academic Press, London, 1977, p. 15.
International Preliminary Report on Patentability issued in PCT Application No. PCT/US2011/049966, dated Mar. 14, 2013.
International Search Report and Written Opinion issued in PCT Application No. PCT/US2011/049966, dated Apr. 9, 2012.
Towe, B.C.: "Use of Piezoelectric Materials as Markers in Ultrasound Imaging", Proceedings of The First Joint BMES/EMBE Conference; Serving Humanity, Advancing Technology, (Oct. 13-16, 1999), 1 page.
Towe, B.C.: "Piezoelectric Contrast Materials for Ultrasound Imaging", IEEE Transactions on Ultrasonics, Ferroelectrics, and Frequency Control, vol. 52, No. 9, (Sep. 2005), pp. 1483-1488.

* cited by examiner

APPARATUS, SYSTEMS, AND METHODS FOR CURRENT MONITORING IN ULTRASOUND POWERED NEUROSTIMULATION

This application is a national phase application under 35 U.S.C. § 371 of International Application No. PCT/US2011/049966 filed 31 Aug. 2011, which claims priority to U.S. Provisional Application No. 61/378,716 filed 31 Aug. 2010. The entire contents of each of the above-referenced disclosures (including the entire disclosure of U.S. patent application Ser. No. 10/524,955 entitled "Neurostimulator" filed Feb. 3, 2006, which was incorporated by reference into the above-referenced PCT Application) is specifically incorporated herein by reference without disclaimer.

BACKGROUND

1. Technical Field

This invention relates to telemetry of human body tissue neurostimulation. More particularly, this invention relates to current monitoring in ultrasound-powered neurostimulation.

2. Description of Related Art

Directly stimulating bioelectrically excitable tissue may be beneficial as a therapeutic tool. For example, neurostimulation may be used for restoring function in cases of neural injury or disease. Neurostimulation as used herein refers to the stimulation of electrically excitable tissues of living things. This can include, for example, the human tissues of the brain, heart, muscle, and nervous system.

Recording biological events may also be beneficial as a therapeutic tool. Tissue bioelectrical events arise from the flow of ionic currents as a result of the action of cellular ionic pumps and channels, which underlie the bioelectrical activity of neural and muscle tissues in the body. These neural and muscle tissues are associated with the function of the brain, muscles, and nervous system. The ionic currents are used for electrocardiograms, electroneurograms, and electromyograms.

Two methods of neurostimulation are the application of pulsed electrical currents directly to tissue through electrodes implanted within tissue and the indirect application of electrical currents through the body surface.

Directly applied electrical currents applied to tissue are known to affect the membranes of excitable cells, causing a depolarizing effect that can lead to a cell action event that depends on its type and biological function. The pulsing of currents is sometimes needed to prevent accommodation to current flows and to fulfill certain physiologic conditions that enables electricity to be effective. Direct application of currents may have the disadvantage of requiring invasive techniques, such as inserting probes or wires into the body.

It is also possible to apply electrical currents to the body surface where they diffuse in the volume conductivity of tissue and attenuate according to well known laws. These currents can also stimulate near-surface nerves and muscle tissues to some degree, but cannot reach deeper tissues because of high electrical losses in tissue and the rise in the needed current levels to above those that would cause electrical shock and tissue damage. It is also difficult to specifically stimulate a particular area of tissue without stimulating surrounding areas.

The strong diffusion of electrical current in tissues from surface electrodes means that specific stimulation of a given nerve or nerve fiber within a bundle is difficult. There is a tendency for electrical currents applied to the body surface to broadly stimulate in undesirable ways. Implantable electrodes overcome these problems but are invasive and suffer from the undesirable need to either run wires through the skin or work with relatively bulky implanted power systems that run on batteries or are powered by external radiofrequency (RF) powering techniques.

In general, techniques that use RF induction to power an implanted device use an inductor implanted within the body that is magnetically coupled to an external RF field. Often this inductor is coupled with a capacitor to form a resonant circuit that is more efficient in coupling to applied RF energy. These devices are relatively large and can be on the order of a centimeter in size.

High frequency currents are not known to stimulate bioelectrically excitable tissues of the nervous system of the body because they are faster than physiologic events can respond. As long as they are relatively high frequency, above several tens of kilohertz and continuing up into the megahertz region currents do not stimulate bioelectrical events or sensations of pain.

A major concern in the development of neurostimulators for implantation near nerve or muscle for therapeutic applications in the human body is the size of the implant. It is preferable that the implanted devices be small and perhaps something that could be introduced into the body through minimally invasive methods, such as syringe needle injection. This is not only for ease of insertion into tissues, but so that they produce less complications such as pressure or force against sensitive tissues as a person moves or exercises. There is also less immunological response and inflammation of tissues with small devices as it reduces their attendant risk of complications. This feature tends to encourage more widespread use in situations which are elective rather than critical.

A neurostimulation device known as a Bion™ has been described which is an example of present methods of designing implantable neurostimulation devices. It is a small cylindrical electrical device which derives its energy from an externally applied RF field. As presently designed, the size of these devices ranges from 6 mm to about 1.5 cm. These devices incorporate active LSI logic and inductive RF powering.

Some versions store energy in batteries or capacitors to deliver later upon digital command and so provide electrical pulses through integral electrodes to neural tissues. These devices are targeted for therapeutic stimulation of muscle and nerves by being implanted within body tissues and in some cases are used for pain relief, treating urinary incontinence, and can be programmed to actuate nerves and muscles in the restoration of lost function in limbs. A disadvantage of these devices is their relative complexity and large size. The large size limits their medical applicability to situations where they can be introduced by surgery or through a large trocar.

The amount of neurostimulation may not always be well know. In some examples, detection of a physiological effect is the only way of knowing whether current has been applied to a bioelectrically excitable tissue. For example, the contraction of a muscle, relief of pain, or firing of a nerve may be used as a sign that current has been applied to bioelectrically excitable tissue. By observing a physiologic response it is often not necessary to be concerned about the exact current flow induced, as long as it is within a range and there are limits to the amount of current that can flow. There are applications of neurostimulation however, such as in stimulation of the esophageal muscle for purposes of gastric reflux monitoring, where the patient may not report any sensation or overt change with effective levels of stimulation.

SUMMARY

A method of measuring neurostimulation is presented. In some embodiments, the method includes providing an ultrasound transmitter near a body surface overlying a piezoelectric device implanted in biological tissue, where the ultrasound transmitter is configured to emit a ultrasound output. The method may also include emitting an ultrasound output from the ultrasound transmitter. In some embodiments, the method further includes creating a rectified current flow from the piezoelectric device in response to the ultrasound output. The method may also include providing a detector, where the detector may be configured to detect an induced current in the biological tissue.

In some embodiments, the rectified current flow from the piezoelectric device may be sufficient to produce neurostimulation in the biological tissue. In some embodiments, the detector may be an electrical current detector configured to measure electrical currents at a surface of the body. However, in some embodiments, the detector may be a radio frequency detector configured to measure a radio frequency signal emitted by the piezoelectric device.

The methods may further comprise determining current flow magnitude in the tissue by comparing a rate of rise of the detected induced current to a linear rise in ultrasound drive level; determining diode voltage; and inferring current flow in the tissue current. Also, the method may comprise determining a reference point by driving a voltage limiting device to maximum with a an intense ultrasound pulse to create a maximal possible signal in the detector; and comparing other surface signals in respective proportion to the maximum.

In some embodiments, the method may include a feedback loop. In some embodiments, the method may include adjusting the ultrasound output in response to the detected current. The method may also include adjusting the amplitude of the ultrasound output in response to the detected current. In some embodiments, the detected current may include more than one measurement of induced current. The induced current may originate in the piezoelectric device. In addition, more than one measurement may be averaged together. In some embodiments, the frequency of the ultrasound output may be adjusted in response to the detected current. In addition, the method may include outputting a signal in response to the detected current. The outputted signal may represent the amount of induced current.

In some embodiments, the biological tissue may include brain tissue, muscle tissue, or nervous system tissue. In some embodiments, the piezoelectric device may include a piezoelectric material and a semiconductor diode. The piezoelectric device may be connected to at least one extended conductor. In some embodiments, the piezoelectric device may be connected to two extended conductors. The extended conductors may allow the piezoelectric device to be spatially separated from the induced current in the biological tissue.

In some embodiments, the ultrasound transmitter may be configured to emit ultrasound waves at a frequency between 20 kHz to 100 MHz. In some embodiments, the ultrasound transmitter may be configured to emit ultrasound waves at a frequency between 100 KHz to 1 MHz. In some embodiments, the ultrasound output may be emitted for a duration short enough that the ultrasound output is no longer being emitted when the induced current is detected. The ultrasound output may be modulated so that it is pulsed for a duration between 1 microsecond and 20 milliseconds.

In some embodiments, the piezoelectric device may be configured to rectify the ultrasound frequency output from ultrasound transmitter. In addition, the piezoelectric device may also include a plurality of diodes. In some embodiments, the plurality of diodes may be arranged in a bridge configuration. In some embodiments the diodes are shunted by a zener diode that limits the maximum voltage that can be produced by the diodes.

An apparatus is also presented. In some embodiments, the apparatus may include an ultrasound transmitter configured to emit an ultrasound output directed at a piezoelectric device implanted in biological tissue. The apparatus may also include a detector configured to detect an induced current in response to the ultrasound output in the biological tissue. The detector may be further configured to report the intensity of the detected induced current.

In some embodiments, the detector may be an electrical current detector configured to measure electrical currents that the surface of the body. In some embodiments, the detector may be a radio frequency detector configured to measure a radio frequency signal emitted by the piezoelectric device. In addition, the detector may be configured to report the intensity of the induced current. The detector may report the intensity of the induced current to a display.

In some embodiments, the apparatus may have a feedback mechanism. In some embodiments, the detector may be configured to report the intensity of the detected current to a feedback controller, where the feedback controller may be configured to adjust the power of the emitted ultrasound output in response to the reported intensity of the detected current. In some embodiments, the feedback controller may be configured to average multiple measurements of detected current. The averaging may be accomplished using a boxcar filter.

In some embodiments, the biological tissue may include brain tissue, muscle tissue, or nervous system tissue. In some embodiments, the piezoelectric device may include a piezoelectric material and one or more semiconductor diode. In some embodiments, the piezoelectric device may be connected to at least one extended conductor.

In some embodiments, the ultrasound transmitter may be configured to emit ultrasound waves at a frequency between 20 KHz to 100 MHz. In some embodiments, the ultrasound transmitter may be configured to emit ultrasound waves at a frequency between 100 KHz to 1 MHz. In some embodiments, the ultrasound output may be modulated so that it is pulsed for a duration between 1 microsecond and 20 milliseconds.

The term "coupled" is defined as connected, although not necessarily directly, and not necessarily mechanically. The terms "a" and "an" are defined as one or more unless this disclosure explicitly requires otherwise. The terms "substantially," "approximately," "about," and variations thereof are defined as being largely but not necessarily wholly what is specified, as understood by a person of ordinary skill in the art. In one non-limiting embodiment, the term substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but it may also be configured in ways other than those specifically described herein.

DETAILED DESCRIPTION OF EXEMPLARY EMBODIMENTS

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
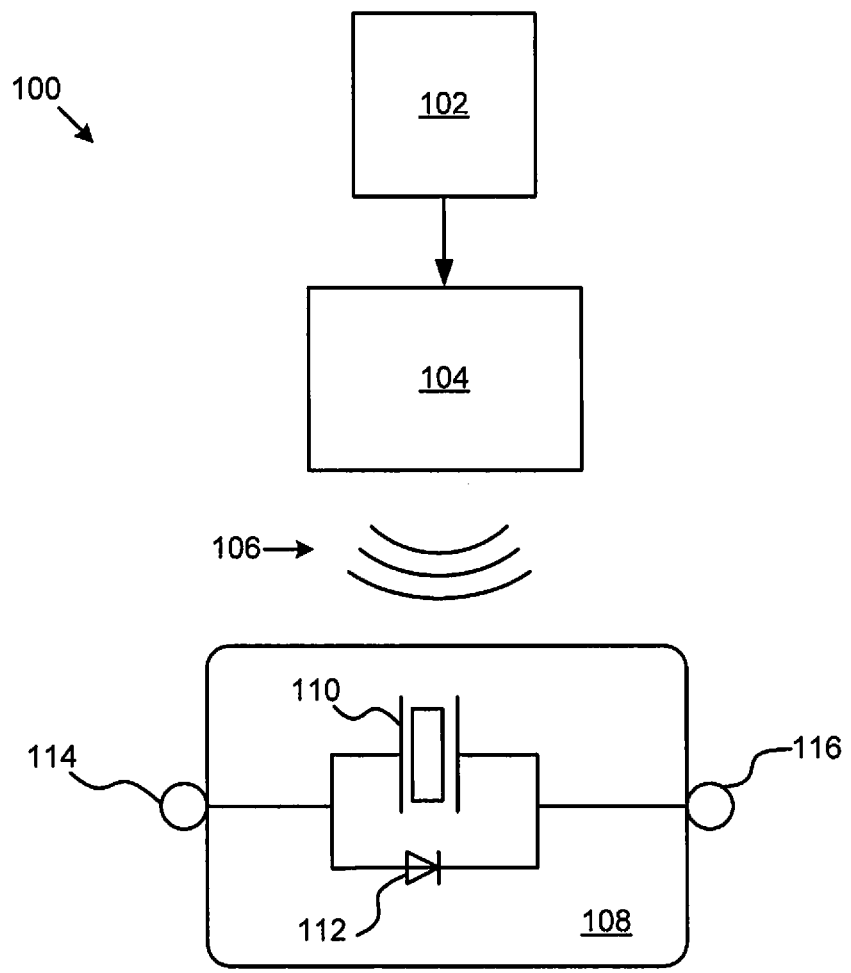
FIG. 1 is a schematic block diagram showing a neurostimulation system that uses a piezoelectric device.

FIG. 1 shows a schematic block diagram of an apparatus 100 for providing neurostimulation. An ultrasound driver 102 is coupled to an ultrasound transmitter 104. The ultrasound driver 102 is configured to cause the ultrasound transmitter 104 to emit an ultrasound output 106. In some embodiments, the ultrasound output can vary in frequency, amplitude, and duration. For example, the ultrasound transmitter 104 may be configured to emit ultrasound waves at a frequency between 20 kHz to 100 MHz. In some embodiments, the ultrasound transmitter 104 may create an output at a frequency between 100 KHz to 1 MHz. The ultrasound output amplitude may also be varied such as making the ultrasound stronger or weaker. In addition, the output may be pulsed on and off. For example, a 1 MHz sine wave may be output from the ultrasound transmitter 104 for a duration of 100 microseconds at a particular amplitude and then turned off (i.e. reduced to an amplitude at or near zero). In some embodiments, the ultrasound output 106 may be pulsed for a duration between 1 microsecond and 20 milliseconds. The pulses may be repeated at a rate of about 1 to 1 kHz. Therefore, an example of a pulsed output may be a 1 MHz signal that lasts for 1 millisecond 100 times every second.

The ultrasound output 106 may excite a piezoelectric device 108 implanted in biological tissue. In some embodiments, the ultrasound output 106 may include a piezoelectric material 110 and a semiconductor diode 112. As shown in FIG. 1, the diode 112 is connected in parallel with the piezoelectric material 110. In some embodiments, the diode 112 may be a Schottky diode, such as an Avago HSMS955 zero-bias diode or a bridge configuration made from such a diode. In some embodiments, the piezoelectric material may be PDVF. One advantage of using a piezoelectric device 108 is its compactness. The piezoelectric device 108 allows targeted neurostimulation with a minimally invasive procedure, such as implantation through a syringe.

The piezoelectric device 108 may be connected to biological tissue through a first electrode 114 and a second electrode 116. An induced current in the piezoelectric device 108 may be transferred to the biological tissue through the first electrode 114 and the second electrode 116. In some embodiments, the induced current may be transferred to the biological tissue and create measurable current (not shown) at the body surface. In some embodiments, the induced current in the piezoelectric device may create radio frequency waves that may propagate out of the body and be detected using a radio frequency receiver. These waves may carry information about the tissue current flow and arise from the rectified piezoelectrically-induced electric wave frequency in the tissue.

Figure 2:
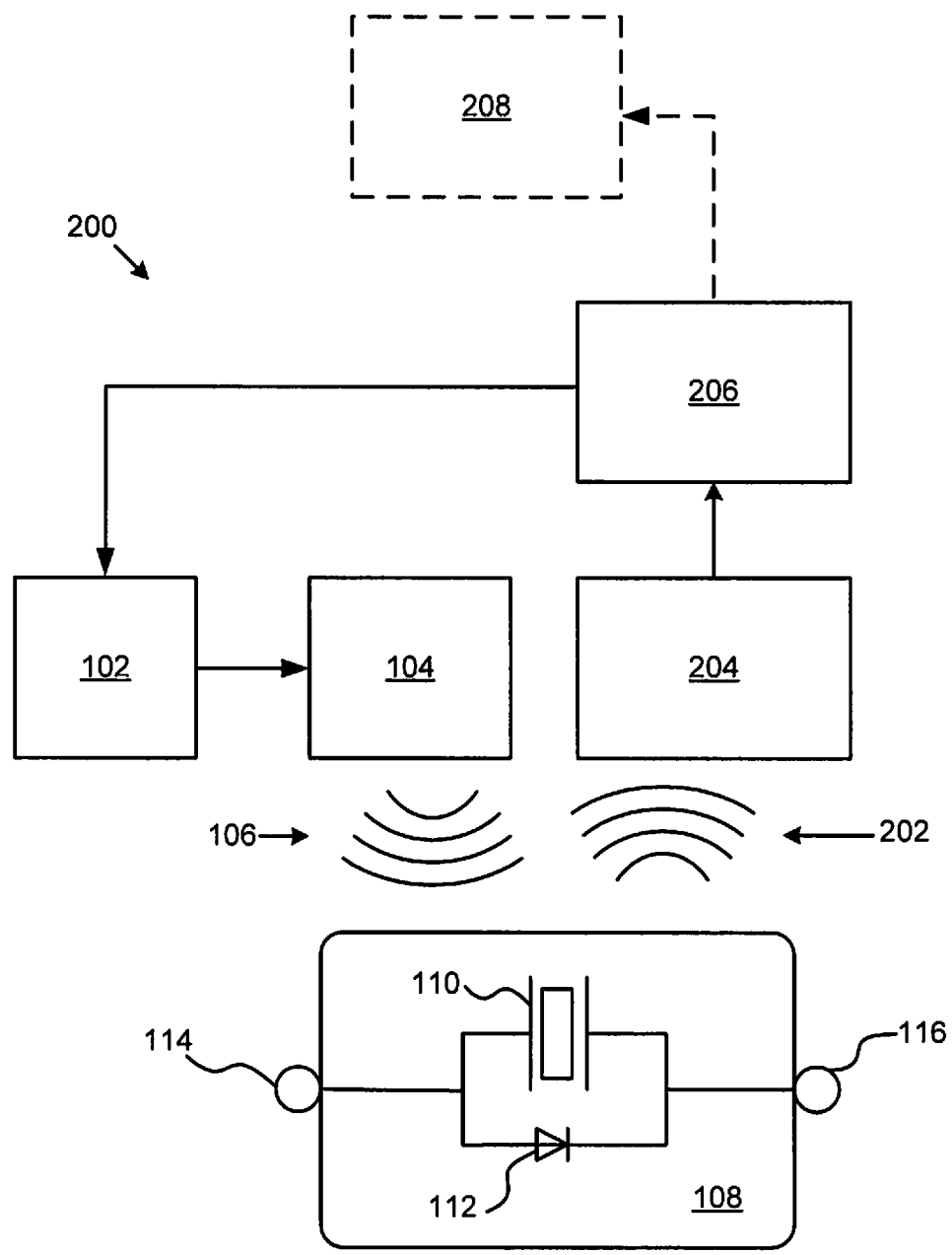
FIG. 2 is a schematic block diagram showing a neurostimulation system with a feedback control loop.

FIG. 2 shows a schematic block diagram of a neurostimulation system 200 that may be used for monitoring or controlling the amount of neurostimulation that is applied to biological tissue. The elements in FIG. 2 that share reference designators with elements in FIG. 1 have the same function as described in connection with FIG. 1. FIG. 2 shows that there is a signal 202 that is created by the induced current in the piezoelectric device 108. The signal 202 may be an electrical signal that is emitted from the first electrode 114 and the second electrode 116, or it may be a radio frequency signal emitted from the piezoelectric device 108. For example, when the diode 112 rectifies a signal created by the ultrasound output 106, diode 112 may emit a signal at the ultrasound frequency or at a second harmonic radio frequency output that has twice the frequency of the ultrasound output 106. By rectifying the signal, the diode 112 creates a pulsating direct current (DC) component to the induced current from the alternating current (AC) excitation of the piezoelectric material 110. The pulsating DC component may be more useful in neurostimulation than an AC signal alone.

Detector 204 is configured to detect the signal 202, which corresponds to the induced current in the biological tissue. The detected signal is therefore representative of the amount of induced current emitting from the piezoelectric device 108. Detector 204 may be a radio frequency receiver configured to detect a signal at the ultrasound frequency or that has twice the frequency of the ultrasound output 106. The detector 204 may also report the detected signal 202 to a feedback controller 206 that determines the amount of induced current based on the strength of the detected signal 202. Another method of detecting strength of the induced current is to observe the rate at which an increase in detected surface current follows the increase in the ultrasound applied amplitude. The diode system having a threshold and non-linear rise of current versus applied piezoelectric voltage gives indicators that are detectable in the currents on the skin as to the diode operating points across the diode and hence stimulating electrodes. The rate of change of the current on the skin for a linear rise in ultrasound drive for example can be used to assess the voltage across the diode rise can be correlated to a diode voltage from the manufacturer's specification sheet. For example the transition point of a diode's characteristic i-v curve whereby it shows a nonlinear forward current at low drive voltages changing to a linear rise in current with higher applied drive voltages can be known from it's published manufacturer specification sheet. Thus this transition point of an implanted diode system can be determined noninvasively by applying a ramp ultrasound drive and observing at what drive level the detected current transitions to a linear rise. This transition point acts as a known current reference point of the diode. Through the use of lookup tables or computation from the diode I-V transfer equation it is thereby possible to infer the current through the diode and thus through tissue stimulating electrodes at other applied ultrasound power levels. The detector 204, or the feedback controller 206 may provide mechanisms to improve the quality of the detected signal. For example, the detector 204 may take and average multiple measurements of the signal 202. Because the signal 202 may comprise many pulses, the detector 204 may be able to take many pulse measurements and measure a detected current that has less noise than any individual measurement. In some embodiments, the feedback controller 206 may output a signal that controls the output of the ultrasound driver 102. This is shows in FIG. 2 as the connection between feedback controller 206 and ultrasound driver 102. The feedback controller 206 may be used to accurately control or monitor the amount of current is induced in the biological tissue. This capability may be important in applications where a physical response is not present or not a reliable indicator of the amount of induced current in the biological tissue. In some embodiments, the feedback controller 206 may optionally be connected to a display 208 (shown in dashed lines). The display 208 may show the amount of current induced in the biological tissue and may be useful in therapeutic applications where a therapist, doctor, or patient may need to see the amount of neurostimulation being applied. Feedback controller 206 may also have an input where the amount of current applied to the biological tissue may be adjusted.

The feedback controller 206 may use analog components such as an operation amplifier, resistors, and capacitors to create the feedback signal. Alternatively, the feedback controller 206 may use a processor coupled to memory to run an algorithm that creates the feedback signal. In some embodiments, the processor used in the feedback controller 206 may be a digital signal processor. The feedback controller 206 may, in some embodiments, use more than one measurement of the detected signal 202 before adjusting the ultrasound output. In one example, the many measurements may be averaged or smoothed using a box car average algorithm or circuit. In one embodiment a box car average such as that produced by EG&G Corp may be used. The neurostimulation system 200 may provide the advantage of making the neurostimulation more controllable in current delivery because the system can determine, and adjust, the current waveform in nearly real-time. This can be particularly beneficial when the stimulators are implanted deeply in the body and the path losses are irregular with body motion, breathing and other physiologic processes. The feedback stabilizes the intensity of the signal by allowing high instantaneous powers where necessary to achieve constant output while maintaining low average powers. Such situations are found for example in stimulation of esophageal sphincter valves located deep from the chest wall surface. Also, the system 200 may allow the user to non-invasively determine the functionality of the piezoelectric device 108, determine the location of the piezoelectric device 108, and detect deterioration of the piezoelectric device 108. These advantages may lead to more effective therapeutic neurostimulation and a safer product for patients.

In some embodiments, ultrasound driver 102, ultrasound transmitter 104, detector 204 and feedback controller 206 may all be in a single enclosure. For example, these elements may be packaged in a small battery powered box with a 1-4 cm diameter piezoelectric transducer. The battery powered box may be strapped to the body, such with an armband around one's arm or a chest band around one's chest.

Calibration of the system 200 may be performed in a number of ways. Using one method, when a piezoelectric device 108 is implanted in biological tissue, a particular amount of current induced in the piezoelectric device may be correlated with a physiological response. For example, when a desired physiological response is observed, the amount of detected signal 202 may be recorded. In subsequent uses, the ultrasound output 106 may be adjusted until the desired level of detected signal 202 is achieved. Using another type of calibration, the ultrasound output 106 required to cause the diode 112 to reach its threshold voltage may be measured. Having a particular amount of current corresponding to an amplitude of ultrasound output 106 can then be used to infer the amount of current induced at other amplitudes of ultrasound output 106.

In some cases, the ultrasound output 106 may make it difficult to accurately measure the detected signal 202 because of transmitter pulse interference. In some embodiments, the ultrasound output 106 and the detected signal 202 may be separated in time to improve the sensitivity of the system 200 to the detected signal. For example the ultrasound output 106 may be emitted for a duration that is equal or less than the time it takes for the ultrasound output 106 to reach the piezoelectric device 108. In this case, by the time that detected signal 202 is emitted (and detected) the ultrasound output 106 is off and therefore not interfering with the measurement of the detected signal. In some embodiments, the short pulses for measuring the amount of induced current can be interspersed between long pulses that may be more suitable for neurostimulation. In addition, the time delay between the ultrasound output 106 and the detected signal 202 may be used to determine the depth of the piezoelectric device 108.

Figure 3:
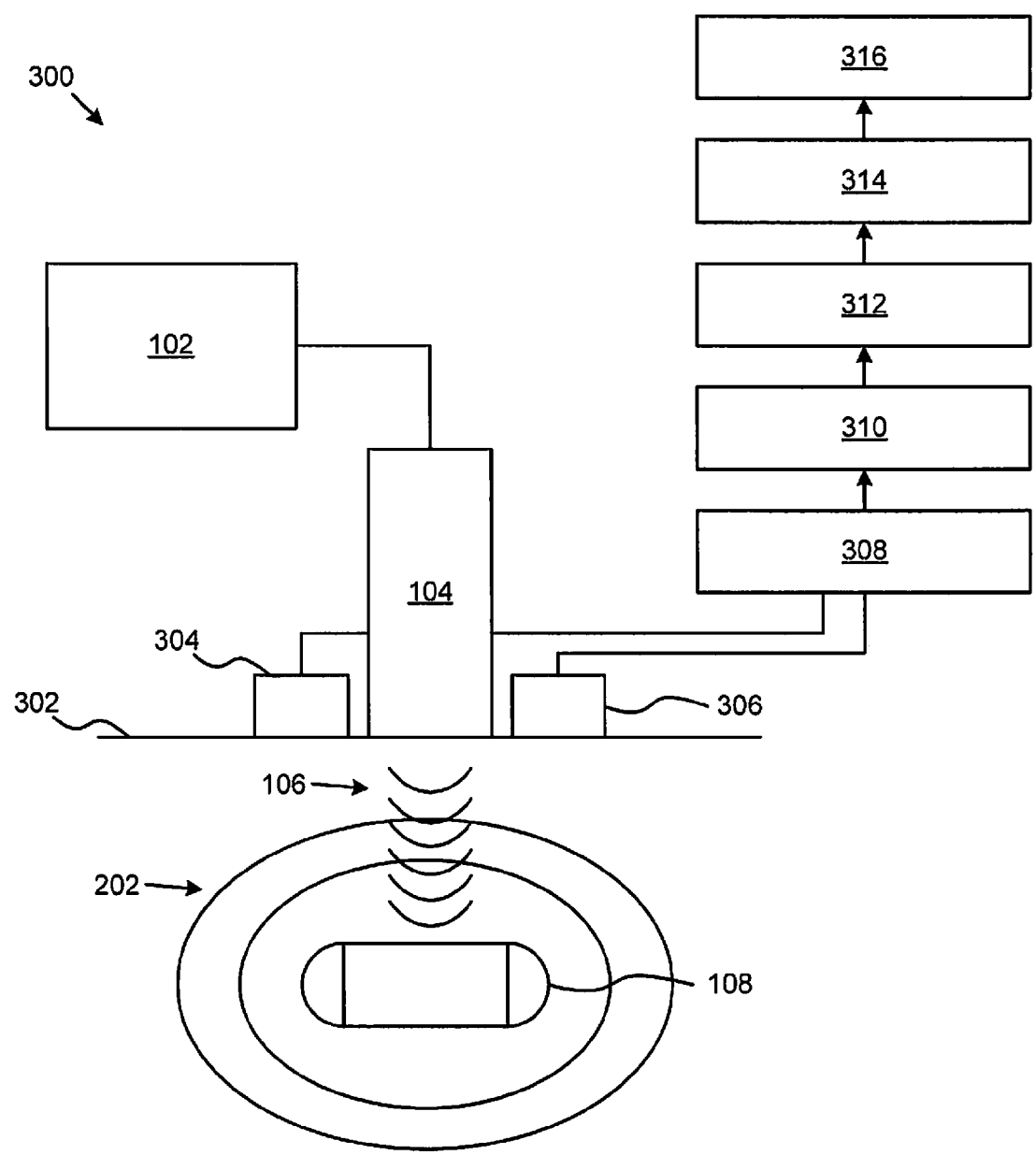
FIG. 3 is a schematic diagram of a piezoelectric device.

FIG. 3 shows a schematic block diagram of a neurostimulation system 300 that may be used for monitoring or controlling the amount of neurostimulation that is applied to biological tissue. The ultrasound driver 102 is coupled to the ultrasound transmitter 104, which causes ultrasound output 106 to be emitted. This figure shows how the ultrasound transmitter 104 is located on the body surface 302. In some embodiments, the ultrasound transmitter 104 may be touching the body surface 302. In some embodiments, the ultrasound transmitter may be near the body surface 302.

The ultrasound output 106 may be directed toward the piezoelectric device 108. The piezoelectric device 108 may then create a rectified current flow 202 between the two electrodes of the piezoelectric device 108. The rectified current flow 202 may then be measured at the body surface 302 by surface electrodes 304 and 306, such as those used for EKGs. In some embodiments, the surface electrodes 304 and 306 may be made of silver-chloride from IVM Corporation. In yet another embodiment, the current flows on the body surface from the implanted device may be detectable by way of an antenna, for, example, a tuned loop of wire, of diameter comparable to the device implantation depth and placed on and parallel to the skin surface. The diameter of the antenna has some variability and still be functional and its design follows rules known to those skilled in the art of radio antenna theory. This antenna approach has the advantage of not requiring the need for contacting electrodes and their associated electrolytes and hence increases patient comfort by replacing them with a simple loop coil that can be applied loosely or suspended a short distance off the skin.

The surface electrodes 304 and 304 may be coupled to a wideband amplifier 308. In some embodiments, the wideband amplifier may be a 100 kHz to 1.3 GHz wideband amplifier as manufactured by Hewlett-Packard Inc. The output of the wideband amplifier 308 may be connected to range gate 310. In some embodiments, the output of the range gate 310 may be coupled to a sample and hold 312. The sample and hold 312 may be used, for example, to detect the peaks of the incoming signal. The output of the sample and hold 312 may be connected to a bandpass filter 314. The band pass filter may be tuned to the frequency of the received signal. The bandpass filter 314 may be connected to a waveform output device 316. For example, the waveform output device may be an LCD screen on an oscilloscope that may be used to monitor the waveform corresponding to the induced current 202. The waveform of this current can be used to determine the diode current flow through in-vivo calibration prior to closure of the implant site. Alternately the current may be determined by digital processing to determine the slope of the waveform rise as a function of increased ultrasound applied amplitude as a way of inferring implanted diode voltage and thus estimation of current flow through prior knowledge of tissue conductivity. In some embodiments, the output device may read out a digital number representing the amplitude of the induced current 202.

Figure 4:
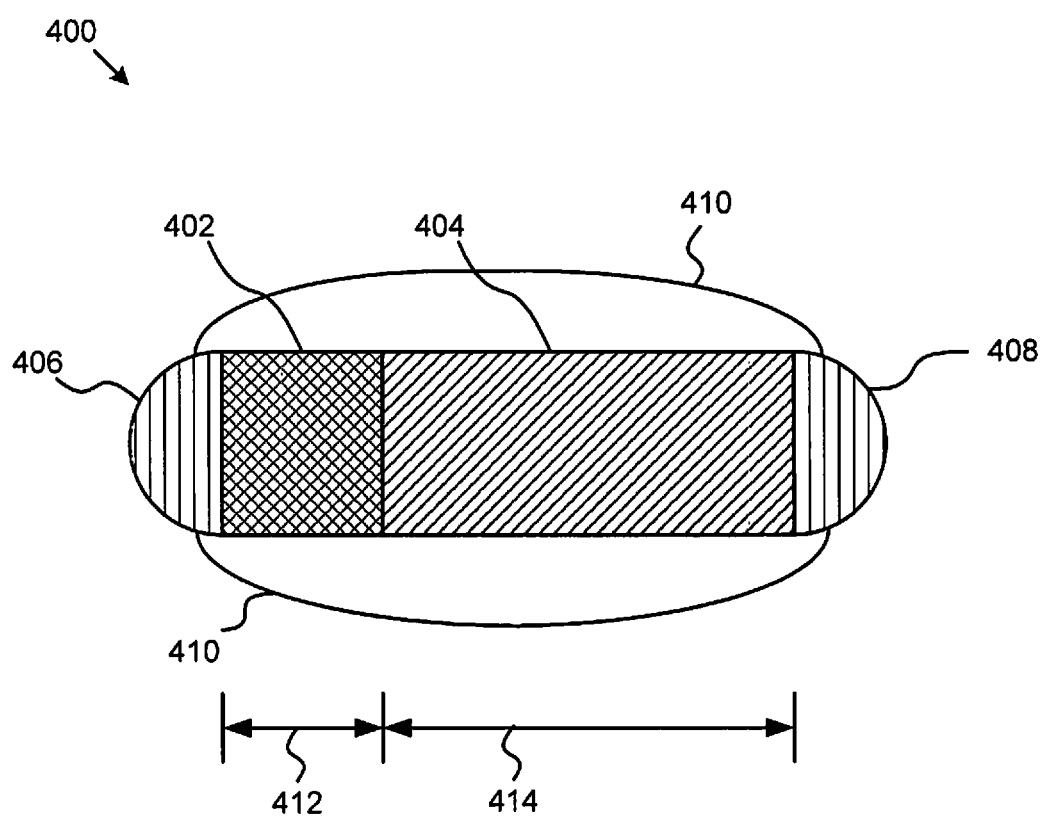
FIG. 4 is a schematic block diagram showing a neurostimulation system.

Turning to FIG. 4, one embodiment of a piezoelectric device 400 is shown. In this embodiment of a piezoelectric device, a diode 402 is coupled to a piezoelectric material 404. In some embodiments, the diode 402 may be a Schottky diode such as an Avago Inc. HSMS955 and the piezoelectric material 404 may be PDVF. In other embodiments the diode may be replaced by a bridge rectifier and yet other embodiments by a voltage multiplier using integral miniature capacitors.

A first electrode 406 and a second electrode 408 may terminate the piezoelectric device 400. In this configuration, the diode 402 and the piezoelectric material 404 may be connected in series or in parallel. If the diode 402 and the piezoelectric material 404 are connected in parallel, a conductor (not shown) may be used to connect together a first end of the diode 402, a first end of the piezoelectric material 404, and the first electrode 406. Similarly, a conductor (not shown) may be used to connect together a second end of the diode 402, a second end of the piezoelectric material 404, and the second electrode 408. The resulting circuit configuration would resemble the piezoelectric material 110 and the diode 112 in the piezoelectric device of FIG. 1. Returning to FIG. 4, in some embodiments, a protective layer 410 may surround and package the piezoelectric device 400. The protective layer 410 may serve to protect the components inside the piezoelectric device 400 from environmental conditions, such as body fluids and immunological responses. In addition, the protective layer 410 may protect the body and biological material from the piezoelectric device 400. For example, the piezoelectric device may contain metals or chemicals that may be harmful to the body if not encapsulated in a protective layer 410. As show in FIG. 4, however, first electrode and second electrode 408 may not be within the protective layer 410 so that they may make an electrical contact with the biological tissue. Electrodes 406 and 408 may be made typically, although not exclusively, of platinum alloyed with iridium. Electrodes 406 and 408 may be alternatively made from tantalum/tantalum pentoxide forming an electrode-capacitor resulting in an ability to do capacitive charge balancing of the stimulation pulse. A capacitor may also be placed in series with the stimulating electrodes to achieve the same effect.

In some embodiments, the piezoelectric device may have an overall length of about 1.0 mm to 6 mm. The diode 402 may have a diode length 412 of about 0.9 mm. The piezoelectric material 404 may have a piezoelectric length 414 of about 1-5 mm. In some embodiments, the piezoelectric device may have an overall length that is less than half of the wavelength of the ultrasound output.

In some embodiments, the amplitude of the detected signal from a piezoelectric device can vary as a function of the orientation and distance between a piezoelectric device and the detector. In some embodiments, multiple sets of orthogonal electrode detectors may be placed on the surface of the skin to enable detection of signals generated by a piezoelectric device. In other embodiments, a piezoelectric device can be used that is polarized in multiple directions so as to create a stimulation effect regardless of the orientations of the implanted device relative to the direction of the ultrasound beam.

In embodiments where more than two detectors are used, differences in the strength or other characteristics of the signals detected by different orientations of detector placements on the skin can be interpreted to locate a plurality of piezoelectric devices relative to each of the individual detectors. In some embodiments, detector positioning and signal processing can be used to locate piezoelectric device in three dimensions. In one embodiment, three separate detectors are placed on the body surface: frontally, saggitally and coronally. This configuration may be similar to the well-known placement called the Frank lead system used for the clinical vectorcardiogram. The detected signals from these body surface detectors could be combined by electrical analog or digital vector addition, prior to being introduced into an ultrasound imaging circuitry. The process for doing this and the resulting imagery generated by this approach can be found in Towe [IEEE Transactions on Ultrasonics, Ferroelectrics, and Frequency Control, 2005, September 52(9) 1483-8.] One advantage of using multiple detectors positioned accordingly is that the resulting piezoelectrical signal can have a constant amplitude regardless of the orientation of the piezoelectric device within the body.

Figure 5:
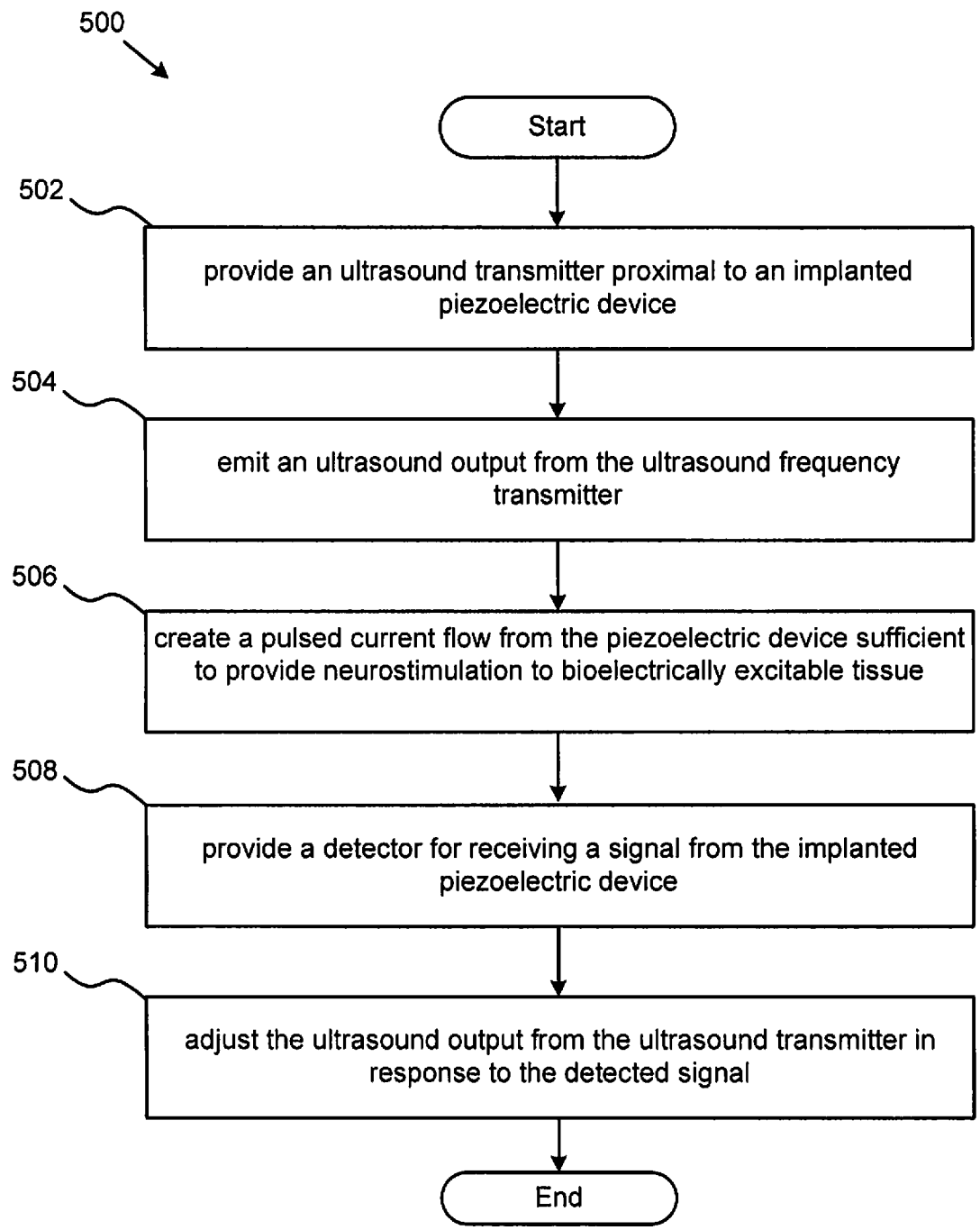
FIG. 5 is a schematic flow chart showing one embodiment of a method for neurostimulation.

FIG. 5 is a flowchart showing one embodiment of a method 500 for applying neurostimulation. Method 500 may begin at step 502 with providing an ultrasound transmitter proximal to a piezoelectric device implanted in biological tissue. In some embodiments, the ultrasound transmitter may overlie the piezoelectric device implanted in biological tissue. In some embodiments, the ultrasound transmitter may be about 2 cm away from the piezoelectric device. In some embodiments, the ultrasound transmitter may be about 10 cm away from the piezoelectric device. The ultrasound transmitter may be configured to emit a ultrasound output in the range of 20 kHz and 100 MHz. In some embodiments, the range may be between 100 kHz and 1 MHz.

In step 504, an ultrasound output is output fro the ultrasound frequency transmitter. The output may change in amplitude and frequency. In addition, the output may be pulsed, meaning that a frequency or range of frequencies is output for a duration of time and then turned off. The pulse length, or duration of the output, may be varied from a few microseconds to a second or more.

In step 506, a pulsed current flow is created from the piezoelectric device that is sufficient to provide neurostimulation to bioelectrically excitable tissue. This may be caused by creating a current flow from the piezoelectric device in response to the ultrasound output. In step 508, a detector is provided that receives a signal from the implanted piezoelectric device. As discussed above, the signal received from the piezoelectric device may be the current measured at the surface of the body. For example, electrodes such as those used for EKGs may be placed on the surface of the body and may detect the current emitting from the piezoelectric device. The signal received from the piezoelectric device may also be a radio frequency signal created inside the piezoelectric device. For example, as the output of a piezoelectric material is rectified by a diode, a signal at the fundamental or the second harmonic signal having twice the frequency of the ultrasound output may emit from the piezoelectric device. Alternately a non-contacting loop antenna or tuned LC circuit coil may be placed in proximity to the skin and the received signal input to a radio frequency receiver optimized in frequency and bandwidth characteristics to detect the pulsed RF frequencies emitted from the tissue In step 510, the ultrasound output from the ultrasound transmitter may be adjusted in response to the detected signal. This step essentially closes the feedback loop and allows the method 500 to actively control the amount of neurostimulation applied to the biological tissue. As discussed above, the feedback loop may be made of analog components such as operational amplifiers. The feedback loop may also be implemented using digital techniques such as digital signal processing and control loop algorithms.

In some embodiments, the amplitude of the ultrasound output may be adjusted in response to the detected signal. In some embodiment, the frequency of the ultrasound output may be adjusted in response to the detected signal.

In some embodiments, the method 500 may also include the step (not shown) of outputting information relating to detected signal. For example, the method may output the detected signal to a display, such as an LCD display, that may allow a technician to monitor the amount of neurostimulation being applied to biological tissue. In some embodiments digital signal processing may be applied so as to determine the current flow produced by the implant through monitoring the rate of surface detected signal change that occur with linear changes in the ultrasound output intensity. Subsequently a look up table or manufacturer's data sheet for the diode(s) can be used to determine implant current flow from the rate of detected signal rise. In some embodiments, the biological tissue may be brain tissue, muscle tissue, or nervous system tissue.

In some embodiments, the piezoelectric device may be connected to an extended conductor. The extended conductor may be, for example, a wire that allows the neurostimulation to be applied in biological tissue that is deep inside a body. In this example, the piezoelectric device may be placed close to the surface of the body, which may allow for efficient transmission of ultrasound energy to the piezoelectric device, while applying the neurostimulation to tissue that is not near the surface of the body. In addition, multiple piezoelectric devices may be placed under the skin in different locations as a way to be selectively activated. For example, extended conductors (wires) may be used to apply neurostimulation from two separate piezoelectric devices to a small area of biological tissue if the piezoelectric devices are separated by a distance. The individual piezoelectric devices may then be individually controlled and may be configured to apply different types of neurostimulation at different periods in time.

In some embodiments of method 500, emitting an ultrasound output from step 504 and detecting the received signal in step 508 are separated by time such that ultrasound output is emitted for a duration short enough that the ultrasound output is no longer being emitted when the induced current is detected. In this fashion, a measured signal from the piezoelectric device is not mixed with the output of the ultrasound transmitter. In some embodiments, the duration of the pulse must be short enough that the time it takes for the ultrasound waves to reach the piezoelectric device is longer than the pulse.

In some embodiments, the ultrasound output is modulated so that it is pulsed for a duration between 1 microsecond and 20 milliseconds. The length of time may be adjusted depending on the amount of neurostimulation required. In some embodiments, the length of time may be adjusted not to provide neurostimulation, but to measure the amount of current being produced in the piezoelectric device. For example, if the ultrasound output is provided for five microsecond, there may not be any significant neurostimulation, but that duration may be long enough to measure the amount of current produced in the piezoelectric device, which can be used to adjust the output from the ultrasound transmitter.

In some embodiments, the piezoelectric device may have multiple diodes arranged in a bridge configuration. A bridge configuration, for example, may be useful in providing full-wave rectification, which may provide more neurostimulation. Additionally, some configurations of diodes may allow for higher voltages to be produced in the piezoelectric device, such as a voltage multiplier circuit. In other configurations, a zener diode or similar voltage limiting element such as a series of diodes, or MOV device may be electrically connected across the electrode system in order to limit the voltage produced by the device and so enhance patient protection against accidental overload.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. An apparatus for providing neurostimulation comprising:
   a piezoelectric neurostimulation device configured to be implanted in biological tissue;
   an ultrasound transmitter configured to emit a ramped ultrasound output directed at the piezoelectric neurostimulation, where the ramped ultrasound output has an amplitude that increases linearly over a period of time;
   where the piezoelectric neurostimulation device comprises a piezoelectric material and a semiconductor diode connected in parallel with the piezoelectric material and the neurostimulation device is configured to generate an induced current in biological tissue in response to the ramped ultrasound output, wherein the induced current provides neurostimulation to the biological tissue;

a non-invasive electrical detector configured to detect the induced current over the period of time and determine a transition in the induced current caused by the semiconductor diode reaching its threshold voltage; and a feedback controller that is configured to calibrate the ultrasound transmitter in response to the transition in induced current detected by the electrical detector.

2. The apparatus of claim 1, where the electrical detector configured to measure electrical currents at the surface of a body.

3. The apparatus of claim 1, where the electrical detector is a radio frequency detector configured to measure a radio frequency signal emitted by the piezoelectric neurostimulation device.

4. The apparatus of claim 3, where the radio frequency signal emitted by the piezoelectric neurostimulation device is a harmonic of a pulse of the ramped ultrasound output.

5. The apparatus of claim 3, where the radio frequency detector is tuned to the radio frequency signal or one of its harmonics.

6. The apparatus of claim 1, where the electrical detector is configured to send a signal that represents the intensity of the induced current to a display.

7. The apparatus of claim 1, where the feedback controller is further configured to average the first plurality of current signals and/or the second plurality of current signals multiple measurements of detected current.

8. The apparatus of claim 1, where the biological tissue comprises brain tissue, muscle tissue, or nervous system tissue.

9. The apparatus of claim 1, where the piezoelectric neurostimulation device is connected to at least one extended conductor that is configured to be in direct contact with the biological tissue.

10. The apparatus of claim 1, where the ultrasound transmitter is configured to emit ultrasound waves at a frequency between 20 kHz to 100 MHz.

11. The apparatus of claim 10 where the ultrasound transmitter is configured to emit ultrasound waves at a frequency between 100 KHz to 1 MHz.

12. The apparatus of claim 1 where the amplitude of the ultrasound output is pulsed for a duration between 1 microsecond and 20 milliseconds.

13. A method of measuring neurostimulation comprising:
providing an ultrasound transmitter proximal to a body surface overlaying a piezoelectric neurostimulation device implanted in biological tissue, where the ultrasound transmitter is configured to emit a ramped ultrasound output and where the piezoelectric neurostimulation device comprises at least a piezoelectric material and a semiconductor diode connected to parallel with the piezoelectric material;

emitting a ramped ultrasound output from the ultrasound transmitter, where the ultrasound output has an amplitude;

creating a current flow from the piezoelectric neurostimulation device in response to the amplitude of ultrasound output;

detecting an induced current in the biological tissue in response to the ramped ultrasound output, wherein the detection may be invasive or non-invasive, and wherein the induced current provides neurostimulation to the biological tissue;

non-invasively detecting the induced current over the period of time and determining a rate of increase of the induced current and a transition in the induced current caused by the semiconductor diode reaching its threshold voltage: and calibrating the ultrasound output from the ultrasound transmitter in response to the transition in the induced current detected.

14. The method of claim 13, where a frequency of the ultrasound output is adjusted in response to the rate of increase of the induced current.

15. The method of claim 13, where the piezoelectric neurostimulation device comprises a piezoelectric material and at least one semiconductor diode or diode array.

16. The method of claim 13, further comprising:
emitting with the ultrasound transmitter a first pulse of the ramped ultrasound output having a duration in the range of 1 to 10 microseconds;

detecting a second induced current in response to the first pulse in the biological tissue; and using the detected second induced current from the first pulse as feedback to control an amplitude and/or duration of a second pulse having a duration in the range of 0.1 to 20 milliseconds sufficient to stimulate the biological tissue.

17. The method of claim 13, wherein detecting the induced current in the biological tissue comprises:
detecting a first current on a skin surface corresponding to a first applied voltage in the piezoelectric neurostimulation device, where the first applied voltage is less than a threshold voltage of a voltage-limiting device; and detecting a second current on the skin surface, where the second current corresponds to a second applied voltage in the piezoelectric neurostimulation device and where the second applied voltage is greater than the threshold voltage of the voltage-limiting device.

* * * * *